United States Patent [19]
Wierzbicki et al.

[11] Patent Number: 5,492,913
[45] Date of Patent: Feb. 20, 1996

[54] N-BENZYLPIPERAZINE COMPOUNDS

[75] Inventors: Michel Wierzbicki, L'Etang la Ville; Jean Lepagnol, Chaudon; Jean-Paul Tillement, Bois le Roi, all of France; Bernard Testa, Lausanne, Switzerland; Yves Rolland, Vanves, France

[73] Assignee: Adir et Compagnie, Courbevoie, France

[21] Appl. No.: 216,795

[22] Filed: Mar. 23, 1994

[30] Foreign Application Priority Data

Mar. 24, 1993 [FR] France .................... 93 03364

[51] Int. Cl.⁶ .................... A61K 31/495; C07D 295/096
[52] U.S. Cl. .................... 514/255; 544/374; 544/398; 544/401
[58] Field of Search .................... 544/398, 401; 514/255

[56] References Cited

U.S. PATENT DOCUMENTS

| | | | |
|---|---|---|---|
| 5,142,053 | 8/1992 | Souvie | 544/398 |
| 5,281,595 | 1/1994 | Lange et al. | 544/401 |
| 5,283,246 | 2/1994 | Regnier et al. | 544/398 |

OTHER PUBLICATIONS

Ohtaka et al, Chem. Pharm. Bull 37 p. 3122 (1989).
Bailey et al, Synlett p. 79 (1994).
Halliwell, et al., Oxygen radicals and the nervous system, TINS, Jan. 1985, pp. 22–26.
Bondy, et al., Review Article entitled: "The Relationship Between Excitotoxicity and Oxidative Stress in the Central Nervous System", Free Radical Biology & Medicine, vol. 14, (1993), pp. 633–642.
Stadtman, Protein Oxidation and Aging, Science, vol. 257, 28 Aug. 1992, pp. 1220–1224.
Bogaert, et al., Original Contribution entitled: "Postischemic Inhibition of Cerebral Cortex Pyruvate Dehydrogenase", Free Radical Biology & Medicine, vol. 16, No. 6, (1994), pp. 811–820.

A. Hartley, et al., Iron induced oxidative stress and mitochondrial dysfunction: relevance to Parkinson's disease, Brain Research 627, (1993), pp. 349–353.
G. Fiskum, et al., LV–4. Brain Protein Oxidation and Inhibition of Pyruvate Dehydrogenase Following Canine Cardiac Arrest and Resuscitation, Journal of Cerebral Blood Flow and Metabolism, The International Society of Cerebral Blood Flow and Metabolism, vol. 13, Suppl. 1 (1993), p. S567.
C. D. Smith, et al., Excess brain protein oxidation and enzyme dysfunction in normal aging and in Alzheimer disease, Proc. Natl. Acad. Sci. USA, vol. 88 (Dec. 1991), Medical Sciences, pp. 10540–10543.
Cao, et al., α–Phenyl–ter–butyl–nitrone reduces cortical infarct and edema in rats subjected to focal ischemia, Brain Research 644 (1994), pp. 267–272.
Carney, et al., Reversal of age–related increase in brain protein oxidation, decrease in enzyme activity, and loss in temporal and spatial memory by chronic administration of the spintrapping compound N–tert–butyl–α–phenylnitrone, Proc. Natl. Acad. Sci. USA, vol. 88 (May 1991), Neurobiology, pp. 3633–3636.
Dean, et al., Hypothesis: a damaging role in aging for reactive protein oxidation products?, Mutation Research 275, (1992), pp. 387–393.
Faden, et al., Pharmacological strategies in CNS trauma, TIPS, Jan. 1992, vol. 13, pp. 29–35.
Hall, et al., Effects of the 21–aminosteroid U74006F on experimental head injury in mice, J Neurosurg 68 (1988), pp. 456–461.

*Primary Examiner*—Emily Bernhardt
*Attorney, Agent, or Firm*—Gordon W. Hueschen

[57] ABSTRACT

The compounds are N-(unsubstituted or substituted) N'-benzylpiperazine compounds and pharmaceutically tolerable salts thereof, useful for treating neuronal disorders resulting from the dysfunctioning of oxidative metabolism.

A compound disclosed is: N-ethyl N'-(2-hydroxy-3,4-dimethoxybenzyl)-piperazine and its dihydrochloride.

7 Claims, No Drawings

N-BENZYLPIPERAZINE COMPOUNDS

The present invention relates to new N-benzylpiperazine compounds, a process for their preparation and pharmaceutical compositions containing them.

It relates especially to compounds of formula

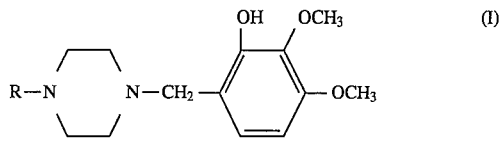

wherein R represents:
1) a hydrogen atom, or
2) a straight-chain or branched alkyl radical containing from 1 to 20 carbon atoms which is optionally mono- or poly-substituted by:
   a a cycloalkyl radical containing from 3 to 7 carbon atoms optionally substituted by a phenyl radical which is itself optionally substituted by one or more halogen atoms or alkyl or alkoxy radicals each having from 1 to 5 carbon atoms,
   b a phenyl radical itself optionally substituted by one or more halogen atoms or alkyl or alkoxy radicals each having from 1 to 5 carbon atoms, or
   c an $OR_1$ radical in which $R_1$ represents:
      a hydrogen atom, or
      a straight-chain or branched alkyl radical containing from 1 to 5 carbon atoms.

The prior art in this field is illustrated especially by:

French Patents 1 302 958 and 805M which relate, respectively, to the preparation of N-trialkoxybenzylpiperazines and the use of 2,3,4-trimethoxybenzylpiperazine as a medicament having a vasodilatory action, the articles by Hiroshi Ohtaka et. al., Chem. Pharm, Bull. 35, 2774–3275 (1987) and Chem. Pharm. Bull. 37, 11, 3122–3124 (1989) which mention trimetazidine compounds having a vasodilatory activity and the synthesis of 1-bis(4-fluorophenyl)methyl]-4-(2-hydroxy-3,4-dimethoxybenzyl)piperazine, and the article by Tsunéo Kawashima et al., J. Pharmacobio-Dyn, 14 449–459 (1991) relating to the isolation and identification of new metabolites of KB-2796 including, inter alia, 1-[bis(4-fluorophenyl)methyl]-4-(2-hydroxy-3,4-dimethoxybenzyl)piperazine.

The compounds of the present invention have a chemical structure which is new compared with that of the closest prior art compounds, and they also have a pharmacological activity and interesting therapeutic properties.

They combat especially the sequelae of disturbances of cerebral oxidative metabolism and more especially the sequelae of hyperoxidation phenomena and peroxidation phenomena (oxidative stress).

They can as a result be used in the treatment of transitory or progressive acute ischaemic syndromes and nervous disorders associated with normal or pathological ageing, such as Alzheimer's disease.

The present invention relates also to a process for the preparation of the compounds of formula I which is characterised in that:

1) A compound of formula I wherein R represents a hydrogen atom is prepared by debenzylation of the corresponding N-benzylated compound. The debenzylation is advantageously carried out by means of hydrogen in the presence of a catalyst, such as, for example, palladium.

2) Compounds of formula I wherein R has one of the meanings given above other than hydrogen are prepared by the action of a reducing agent on compounds of formula II:

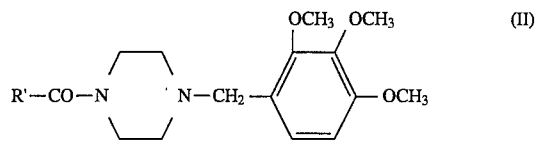

wherein R' represents:
a a hydrogen atom;
b a phenyl radical optionally substituted by one or more halogen atoms or by one or more alkyl or alkoxy radicals each having from 1 to 5 carbon atoms;
c a cycloalkyl radical having from 3 to 7 carbon atoms optionally substituted by a phenyl radical which is itself optionally substituted by one or more halogen atoms or by one or more alkyl or alkoxy radicals each having from 1 to 5 carbon atoms; or
d a straight-chain or branched alkyl radical containing from 1 to 19 carbon atoms which is optionally mono- or poly-substituted by:
   α a cycloalkyl radical having from 3 to 7 carbon atoms optionally substituted by a phenyl radical which is itself optionally substituted by one or more halogen atoms or by one or more alkyl or alkoxy radicals each having from 1 to 5 carbon atoms;
   β a phenyl radical, itself optionally substituted by one or more halogen atoms or by one or more alkyl or alkoxy radicals each having from 1 to 5 carbon atoms; or
   τ a radical selected from the groups of formulae:
   —O—$COR_3$, —$COOR_3$ and

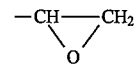

(wherein $R_3$ represents a hydrogen atom or an alkyl radical containing from 1 to 5 carbon atoms), according to whether it is desired to prepare a compound of formula I in which the substituent R contains, respectively, a

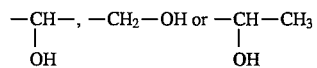

group.

Thus, in the compound II, reduction of the CO function bonded to the piperazine nucleus and almost exclusive demethylation of the methoxy group in the 2-position of the trimethoxybenzyl group are achieved simultaneously.

The compound I so obtained may be purified according to conventional physical and chemical methods.

The starting materials of formula II were prepared by the acylation of trimetazidine.

The compounds of formula I may be converted into addition salts with acids, which salts, as such, form part of the present invention. There may be mentioned as acids for the formation of those salts, for example, in the inorganic series, hydrochloric, hydrobromic, sulphuric, nitric and phosphoric acid and, in the organic series, acetic, propionic, maleic, fumaric, tartaric, oxalic, benzoic, methanesulphonic and isethionic acid.

The compounds of formula I are oils or crystalline compounds having a low melting point. It is therefore useful to synthesise their salts (generally mono- or di-hydrochlorides) to obtain crystalline products that are soluble in water.

The compounds of formula I and the physiologically tolerable addition salts thereof have valuable pharmacological and therapeutic properties.

It is well known that in the course of physiological or pathological cerebral ageing (dementias) and during cerebral accidents, the neurones are especially vulnerable to disturbances of oxidative metabolism and especially to phenomena of reactive hyperoxidation or oxidative stress. It is for that reason that the formation of oxygenated free radicals is considered as one of the causes of acute or progressive neurone death.

This special vulnerability of neurones to peroxidation processes can be explained in part by the strong concentrations of iron and ascorbate present in the brain and by the low cerebral levels of antioxidising enzymes.

The pathological phenomena associated with hyperoxidation affect both the cellular lipid structures and the membrane and cytosolic proteins. They result in structural disorganisation, which has been demonstrated both in the course of cerebral ageing and in the course of acute ischaemia.

It is possible to show by means of experiments the pernicious effects of hyperoxygenation-hyperoxidation both in vitro and in vivo.

It is for that reason that the compounds of the present invention have been rationally and preferentially studied in vivo in a model of convulsions induced by hyperbaric oxygenation and in a model of cerebral concussion in mice. The two models were selected for their capacity to bring into play cerebral hypermetabolism phenomena, and thus oxidative stress, the behavioural sequelae of which can be attenuated by the reference compounds, so-called free radical scavengers, or conversely aggravated by agents that promote peroxidation phenomena.

Under those conditions, the compounds of the present invention demonstrated significant protective effects against experimental cerebral aggression. Those effects were obtained at lower doses than, and with a cerebral bioavailability far superior to, the prior art compounds used as reference compounds.

By clearly combating the pernicious phenomena associated with the diversion of the physiological use of oxygen, the compounds of the present invention can be used therapeutically in the treatment of neurone diseases resulting from the dysfunction of oxidative metabolism and especially from cellular oxidative stress. Those neuronal pathologies, which can be of central, peripheral or medullar origin, cause acute or progressive neurone death. They include, for example, constitutional or transitory ischaemia, traumas, cerebral ageing, and neurodegenerative diseases such as, for example, Alzheimer's disease, Parkinson's disease, Pick's disease and Huntington's disease.

The present invention also relates to pharmaceutical compositions comprising as active ingredient a compound of formula I or a physiologically tolerable salt thereof, mixed with or in association with an appropriate pharmaceutical excipient.

The so-obtained pharmaceutical compositions are generally presented in dosage form and may contain from 0.1 to 300 mg of active ingredient.

They may, for example, be in the form of tablets, dragées, gelatin capsules, suppositories or injectable or drinkable solutions, and may be administered by the oral, rectal, intravenous or parenteral route.

The dosage varies in accordance with the age and weight of the patient, the route of administration, the nature of the disorder and associated treatments, and generally ranges from 0.1 to 300 mg of active ingredient from 1 to 3 times per day.

The following Examples illustrate the present invention.

A Preparation of the Starting Materials of Formula II by the acylation of trimetazidine. Preparation of N-benzoyltrimetazidine

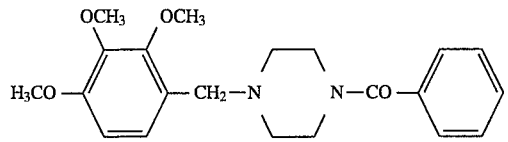

53.2 g (0.2 mol) of trimetazidine in 400 ml of diethyl ether and 14 g (0.1 mol) of benzoyl chloride in 400 ml of diethyl ether are simultaneously added to a reactor at room temperature with vigorous stirring. When the addition is complete, the stirring is continued for a further 3 hours and the mixture is then filtered. The residue is washed three times with 200 ml of diethyl ether each time. The ethereal phase is dried and the solvent is removed by distillation, yielding a first fraction of 29 g. The filtration residue is dissolved in 300 ml of water. The aqueous phase is extracted twice with 200 ml of diethyl ether each time. 3.7 g are recovered in a second fraction and added to the first fraction, thus giving 32.7 g of N-benzoyltrimetazidine (yield: 88 %).

The following were obtained using the same procedure:
N-formyltrimetazidine,
N-acetyltrimetazidine,
N-propionyltrimetazidine,
N-isobutyryltrimetazidine,
N-butyryltrimetazidine,
N-hexylcarbonyltrimetazidine,
N-pentadecylcarbonyltrimetazidine,
N-heptadecylcarbonyltrimetazidine,
N-(3-ethoxycarbonylpropionyl)-trimetazidine,
N-(4-ethoxycarbonyl-3,3-dimethylbutyryl)-trimetazidine,
N-phenylcyclopropylcarbonyltrimetazidine,
N-(7-ethoxycarbonylheptanoyl)-trimetazidine.

B/Preparation of Compounds of Formula I

EXAMPLE 1

N-ethyl-N'-(2-hydroxy-3,4-dimethoxybenzyl)-piperazine:

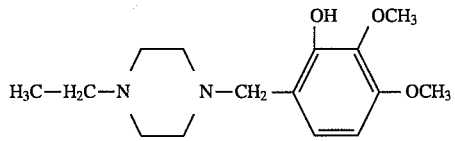

30.8 g (0.1 mol) of N-acetyltrimetazidine, 600 ml of diethyl ether and 11.1 g (0.3 mol) of LiAlH$_4$ are heated to and then maintained at reflux for 24 hours with vigorous stirring, the mixture is subsequently allowed to return to room temperature, and stirring is continued for a further 12 hours, after which the mixture is hydrolysed in succession with 10 ml of water, 10 ml of 4N sodium hydroxide solution and finally 30 ml of water. The mixture is filtered and the residue is washed three times with 200 ml of diethyl ether each time. The ethereal phases are removed and the residue is then taken up three times with 300 ml of CH$_2$C$_2$ each time. The organic phase obtained after filtration is dried over magnesium sulphate, and the solvent is then removed by evaporation in vacuo. The residue (approximately 20 g) is filtered over 150 g of silica using a mixture of chloroform and ethanol (97.5% –2.5%) as eluants. 18 g of N-ethyl-N'-(2-hydroxy-3,4-dimethoxybenzyl)-piperazine are obtained directly (yield: 64%).

0.01 mol of the compound so obtained dissolved in the minimum amount of anhydrous diethyl ether is added to twice the stoichiometric amount of HCl dissolved in diethyl ether. An abundant precipitate immediately forms. It is recovered by filtration and recrystallised from a mixture of ethanol and diethyl ether to yield the dihydrochloride of N-ethyl-N'-(2-hydroxy-3,4-dimethoxybenzyl)-piperazine, m.p. >250° C.

EXAMPLES 2 to 13:

The compounds given as examples in the following were prepared by proceeding in accordance with the method described in Example 1:

2) N-methyl-N'-(2-hydroxy-3,4-dimethoxybenzyl)-piperazine and its dihydrochloride, m.p. >230° C. with decomposition (diethyl ether).
3) N-propyl-N'-(2-hydroxy-3,4-dimethoxybenzyl)-piperazine and its dihydrochloride, m.p.: 230°–232° C.
4) N-butyl-N'-(2-hydroxy-3,4-dimethoxybenzyl)-piperazine and its dihydrochloride, m.p.: 240° C. with sublimation.
5) N-isobutyl-N'-(2-hydroxy-3,4-dimethoxybenzyl)-piperazine and its dihydrochloride, m.p.: 225° C.
6) N-heptyl-N'-(2-hydroxy-3,4-dimethoxybenzyl)-piperazine and its dihydrochloride, m.p.: 217° C.
7) N-hexadecyl-N'-(2-hydroxy-3,4-dimethoxybenzyl)-piperazine and its dihydrochloride, m.p.: 206–210° C. (isopropanol).
8) N-octadecyl-N'-(2-hydroxy-3,4-dimethoxybenzyl)-piperazine and its dihydrochloride, m.p.: 221° C. (diethyl ether).
9) N-(4-hydroxybutyl)-N'-(2-hydroxy-3,4-dimethoxybenzyl)-piperazine and its dihydrochloride, m.p. >228° C. with sublimation (diethyl ether).
10) N-(7-hydroxyoctyl)-N'-(2-hydroxy-3,4-dimethoxy-benzyl)-piperazine and its dihydrochloride, m.p. >210° C. with decomposition.
11) N-(5-hydroxy-3,3-dimethylpentyl)-N'-(2-hydroxy-3,4-dimethoxybenzyl)-piperazine and its dihydrochloride, m.p. >240° C. with sublimation.
12) N-benzyl-N'-(2-hydroxy-3,4-dimethoxybenzyl)-piperazine and its dihydrochloride, m.p. >240° C. with sublimation (diethyl ether).
13) E-N-[(2-phenylcyclopropyl)methyl]-N'-(2-hydroxy-3,4-dimethoxybenzyl)-piperazine and its dihydrochloride, m.p.: 212° C. (isopropanol/water).

EXAMPLE 14

N-(2-hydroxy-3,4-dimethoxybenzyl)-piperazine:

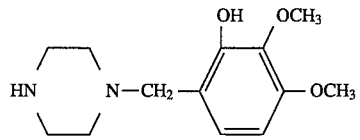

6.8 g (0.02 mol) of N-benzyl-N'-(2-hydroxy-3,4-dimethoxybenzyl)-piperazine are dissolved in 200 ml of ethanol at 60° C. 1.1 g of 5% palladium on carbon are added thereto and the whole is hydrogenated under a pressure of 5,500 hPa, after which the alcoholic solution is filtered and the solvent is distilled off. The oil obtained is chromatographed on 150 g of silica. A first elution with dichloromethane removes the lower polarity impurities from the mixture. The silica is then washed with a $CH_2C_2/CH_3OH$ mixture (90/10). 3.78 g of N-(2-hydroxy-3,4-dimethoxybenzyl)-piperazine are obtained (60% yield), and the compound is then converted into its dihydrochloride (m.p. >190° C.) by adding twice the stoichiometric amount of HCl.

c/PHARMACOLOGICAL STUDY

EXAMPLE 15

A) Principle

Disturbances of oxidative metabolism and more especially oxidative stress are considered to be one of the major causes of acute or progressive neurone death. The diversion of the physiological use of oxygen to the formation of oxygenated free radicals causes a disorganisation of both lipid and protein cellular structure.

It has since been well demonstrated that those peroxidation phenomena are characteristic of normal cerebral ageing, of cerebral ageing of the dementia type, and of cerebrovascular accidents.

Hyperbaric oxygenation in vivo makes it possible to reproduce oxidative stress experimentally and in an accelerated way, the oxidative stress being manifested in mice by convulsive fits which may result in death. Under those conditions the antioxidising protective agents (glutathione, scavengers) delay the onset of the convulsive fit whereas the pro-oxidising agents ($H_2O_2$, ascorbate, $Fe^{++}$) promote it.

In the same way, non-traumatising cranial shock brings about a reactive hypermetabolism which manifests itself as a convulsive fit. The fit leads to a transitory coma phase, the duration of which can be reduced by the antioxidising protective agents (scavengers).

The compounds of the invention were studied in the above two tests (hyperbaric oxygenation, cerebral concussion) according to the central route of administration (i.c.v.: intracerebroventricular) or peripheral routes of administration (i.v. : intravenous; i.p. : intraperitoneal) for the purpose of studying their degree of intracerebral bioavailability in addition to the intensity of their pharmacological effects.

b) Methodology

Hyperbaric oxygenation in mice

Male CD1 mice (Charles River) are placed individually in impervious boxes which are circulated with a stream of pure oxygen at a pressure of 6 atmospheres. The time taken for a generalised tonoclonic fit to occur is noted for each animal. Under those conditions, the fit occurs after 17 to 18 minutes in the case of the control animals. For each of the compounds studied, the average time taken for the fit to occur is compared with that of a control group receiving only the solvent. An $ED_{50}$, prolonging by 50% the time taken for a fit to occur, is thus determined for each compound. The compounds are studied by the i.c.v. administration of 5 µl (doses in mg/animal), or the i.v. administration of 5 ml/kg (doses in mg/kg), 30 minutes before the test.

Concussion in mice

Conscious male CD1 mice (Charles River) are immobilised at the level of the cranium by a vertical metal bar ending in a teflon tip. A weight sliding around the bar is fixed at a height of 12 cm and the impact of that weight on the teflon end reverberates on the cranial arch of the animal. The impact causes a convulsive fit, then a coma, and sometimes the death of the animals. The time taken before spontaneous movement commences again is noted. In the case of the control animals, that time is approximately 250 seconds.

A protection index is calculated as the median coma time of the animals for each dose of compound studied.

The $ED_{66}$ which reduces the median coma time by 66% is determined for each compound studied.

The compounds are studied by i.p. administration at a volume of 20 ml/kg (dose in mg/kg) 30 minutes before the test.

c) Results

Hyperbaric oxygenation in mice

Under our severe conditions of oxidative stress, the compounds of the present invention exert protective effects that are far more valuable than those of the reference compounds whether from the prior art, trimetazidine, or from among the most powerful free radical scavengers, U78517F (lazaroide).

In fact, although they exert comparable effects when administered i.c.v., their protective effects when administered i.v., the therapeutic administration route, are far superior, and the relationship of the i.v./i.v.c. effective doses shows that they possess a much better cerebral bioavailability. In addition, those effects are exerted according to a linear dose-effect relationship over a wide range of doses, which is not true especially of trimetazidine for which the range of active doses is very narrow and biphasic.

The following Table lists those results :

|  | $ED_{50}$ i.v. | $\dfrac{ED_{50}\ i.v.}{ED_{50}\ i.c.v}$ | Dose-effect relationship |
|---|---|---|---|
| Trimetazidine | 2 | 25 | biphasic |
| U78517F | 5 | 16 | linear |
| Example 10 | 0.5 | 1 | linear |
| Example 13 | 0.2 | 1 | linear |
| Example 14 | 0.6 | 6 | linear |

Cerebral concussion in mice

As in the above test, the compounds of the invention exert protective effects at weaker doses than those of the reference compounds. Those effects are also manifested according to a linear dose-effect relationship, which, again, is not the case with trimetazidine, which is significantly active at one dose only (3 mg/kg i.p.).

|  | $ED_{66}$ | dose-effect relationship | range of active doses |
|---|---|---|---|
| trimetazidine | 1 | biphasic | 1 and 3 |
| U78517F | 3 | linear | 3 and 10 |
| Example 1 | 0.2 | linear | 0.1 to >3 |
| Example 10 | 0.2 | linear | 0.1 to >3 |
| Example 14 | 0.5 | biphasic | 0.1 to 3 | d) Conclusion

The compounds of the invention are clearly distinguished from the reference compounds in the intensity of their pharmacological effects, which are are exhibited as a result of a preferential cerebral tropism and are according to a linear and thus pharmacological dose-effect relationship. Those effects are superior to those of the prior art compounds and also to those compounds known to be most active against cellular disorders resulting from hyperoxidation and oxidative stress.

The compounds of the invention thus constitute novel therapeutic agents for the avoidance and limitation of acute or progressive neurone death.

We claim:

1. An N-benzylpiperazine compound selected from those of formula I:

$$R-N\diagup\diagdown N-CH_2-\text{(2-hydroxy-3,4-dimethoxyphenyl)} \quad (I)$$

wherein R represents:
  straight-chain or branched alkyl having inclusive 1 to 20 carbon atoms which is optionally mono- or poly-substituted by:
    a. cycloalkyl having 3 to 7 carbon atoms inclusive, unsubstituted or substituted by phenyl which is unsubstituted or substituted by one or more halogen atoms or by alkyl or alkoxy each having 1 to 5 carbon atoms inclusive, or by
    $OR_1$ in which $R_1$ represents:
    b. hydrogen or
    straight-chain or branched alkyl having 1 to 5 carbon atoms inclusive;
and pharmceutically-acceptable acid addition salts thereof.

2. A compound of claim 1 which is selected from: N-ethyl-N'-(2-hydroxy-3,4-dimethoxybenzyl)-piperazine · and its dihydrochloride.

3. A compound of claim 1 which is selected from: N-(7-hydroxyoctyl)-N'-( 2-hydroxy-3,4-dimethoxybenzyl)-piperazine and its dihydrochloride.

4. A compound of claim 1 which is selected from : E-N-[( 2-phenylcyclopropyl)methyl]-N'-(2-hydroxy-3,4-dimethoxybenzyl)-piperazine and its dihydrochloride.

5. A compound of claim 1 selected from the group consisting of:
N-ethyl-N'-(2-hydroxy-3,4-dimethoxybenzyl)-piperazine,
N-methyl-N'-(2-hydroxy-3,4-dimethoxybenzyl)-piperazine and its dihydrochloride,
N-propyl-N'-(2-hydroxy-3,4-dimethoxybenzyl)-piperazine and its dihydrochloride,
N-butyl-N'-(2-hydroxy-3,4-dimethoxybenzyl)-piperazine and its dihydrochloride,
N-isobutyl-N'-(2-hydroxy-3,4-dimethoxybenzyl)-piperazine and its dihydrochloride,
N-heptyl-N'-(2-hydroxy-3,4-dimethoxybenzyl)-piperazine and its dihydrochloride,
N-hexadecyl-N'-(2-hydroxy-3,4-dimethoxybenzyl)-piperazine and its dihydrochloride,
N-octadecyl-N'-(2-hydroxy-3,4-dimethoxybenzyl)-piperazine and its dihydrochloride,
N-(4-hydroxybutyl)-N'-(2-hydroxy-3,4-dimethoxybenzyl)-piperazine and its dihydrochloride,
N-(7-hydroxyoctyl)-N'-(2-hydroxy-3,4-dimethoxybenzyl)-piperazine and its dihydrochloride,
N-(5-hydroxy-3,3-dimethylpentyl)-N'-(2-hydroxy-3,4-dimethoxybenzyl)-piperazine and its dihydrochloride, and
E-N-[(2-phenylcyclopropyl)methyl]-N'-(2-hydroxy-3,4-dimethoxybenzyl)-piperazine and its dihydrochloride.

6. A pharmaceutical composition useful for treating neuronal disorders resulting from the dysfunctioning of oxidative metabolism, comprising as active ingredient an effective amount of a compound of claim 1 together with a pharmaceutically-acceptable excipient.

7. A method for treating a mammal afflicted with a neuronal disorder selected from ischaemias and traumas resulting from the dysfunctioning of oxidative metabolism, comprising the step of administering to the said mammal an amount of a compound of claim 1 which is effective for alleviation of the said disorder.

* * * * *

UNITED STATES PATENT AND TRADEMARK OFFICE
CERTIFICATE OF CORRECTION

PATENT NO. : 5,492,913  
DATED : Feb. 20, 1996  
INVENTOR(S) : Michel Wierzbbicki, Jean Lepagnol, Jean-Paul Tillement, Bernard Testa, Yves Rolland Page 1 of ?

It is certified that error appears in the above-indentified patent and that said Letters Patent is hereby corrected as shown below:

Column 1, line 39: "1-bis" should read -- 1-[bis --.

Column 4, line 6: Should read -- A/PREPARATION OF THE STARTING MATERIALS OF FORMULA II --.

Column 4, line 7: Delete "II" from beginning of the line.

Column 4, line 43: Should read -- B/PREPARATION OF COMPOUNDS OF FORMULA I --.

Column 4, line 66: "$CH_2C_2$" should read -- $CH_2Cl_2$ --.

Column 6, line 4: "$CH_2C_2$/should read -- $CH_2Cl_2$/ --

Column 8, line 24: Add -- b. -- to beginning of the line.
<u>Claim 1, line 18</u>.

UNITED STATES PATENT AND TRADEMARK OFFICE
CERTIFICATE OF CORRECTION

PATENT NO. : 5,492,913
DATED : Feb. 20, 1996
INVENTOR(S) : Michel Wierzbbicki, Jean Lepagnol, Jean-Paul Tillement, Bernard Testa, Yves Rolland It is certified that error appears in the above-indentified patent and that said Letters Patent is hereby corrected as shown below:

Column 8, line 25: Delete "b." from the beginning of the line.

Column 8, line 36: Delete spaces after "[(".

Column 8, line 58: Delete spaces before "3,4-".

Column 8, line 61: Delete spaces before "3,4-".

Signed and Sealed this

Twenty-first Day of May, 1996

*Attest:*

BRUCE LEHMAN

*Attesting Officer*     *Commissioner of Patents and Trademarks*